(12) United States Patent
Stern et al.

(10) Patent No.: US 7,909,770 B2
(45) Date of Patent: Mar. 22, 2011

(54) METHOD FOR USING A WIRELESS PRESSURE SENSOR TO MONITOR PRESSURE INSIDE THE HUMAN HEART

(75) Inventors: David R. Stern, Grayson, GA (US); Jason White, Decatur, GA (US); Miguel Luis Berr, Santiago (CL); Kevin Corcoran, Mableton, GA (US)

(73) Assignee: CardioMEMS, Inc., Atlanta, GA (US)

( * ) Notice: Subject to any disclaimer, the term of this patent is extended or adjusted under 35 U.S.C. 154(b) by 0 days.

(21) Appl. No.: 11/773,083

(22) Filed: Jul. 3, 2007

(65) Prior Publication Data

US 2008/0082005 A1 Apr. 3, 2008

Related U.S. Application Data

(60) Provisional application No. 60/818,707, filed on Jul. 5, 2006.

(51) Int. Cl.
*A61B 5/02* (2006.01)
(52) U.S. Cl. .......................................... 600/486; 600/485
(58) Field of Classification Search .................. 600/481, 600/483–488, 508, 561; 607/60, 17, 18, 607/19, 23–26
See application file for complete search history.

(56) References Cited

U.S. PATENT DOCUMENTS

| | | | |
|---|---|---|---|
| 6,015,386 A * | 1/2000 | Kensey et al. ................ | 600/486 |
| 6,024,704 A * | 2/2000 | Meador et al. ................ | 600/486 |
| 6,078,835 A * | 6/2000 | Hedberg et al. ............... | 607/9 |
| 6,141,588 A * | 10/2000 | Cox et al. ........................ | 607/9 |
| 6,409,674 B1 * | 6/2002 | Brockway et al. ............ | 600/486 |
| 6,855,115 B2 * | 2/2005 | Fonseca et al. ............... | 600/488 |
| 6,926,670 B2 * | 8/2005 | Rich et al. ..................... | 600/459 |
| 7,267,649 B2 * | 9/2007 | Zdeblick et al. .............. | 600/301 |
| 7,425,200 B2 * | 9/2008 | Brockway et al. ............ | 600/486 |
| 7,481,771 B2 * | 1/2009 | Fonseca et al. ............... | 600/486 |
| 2002/0120200 A1 * | 8/2002 | Brockway et al. ............ | 600/488 |
| 2002/0138009 A1 * | 9/2002 | Brockway et al. ............ | 600/485 |
| 2003/0139677 A1 * | 7/2003 | Fonseca et al. ............... | 600/508 |
| 2004/0111006 A1 * | 6/2004 | Alferness et al. ............. | 600/16 |
| 2004/0215049 A1 * | 10/2004 | Zdeblick et al. .............. | 600/16 |
| 2005/0015014 A1 * | 1/2005 | Fonseca et al. ............... | 600/488 |
| 2005/0182330 A1 * | 8/2005 | Brockway et al. ............ | 600/486 |
| 2005/0288727 A1 * | 12/2005 | Penner ........................... | 607/32 |
| 2006/0047205 A1 * | 3/2006 | Ludomirsky et al. ......... | 600/486 |
| 2006/0287602 A1 * | 12/2006 | O'Brien et al. ................ | 600/486 |

\* cited by examiner

*Primary Examiner* — Charles A Marmor, II
*Assistant Examiner* — Navin Natnithithadha
(74) *Attorney, Agent, or Firm* — Ballard Spahr LLP

(57) ABSTRACT

A method for measuring pressure within a heart includes the steps of: (1) providing a passive wireless pressure sensor having a characteristic impedance and a deflectable surface, the characteristic impedance changing in response to deflection of the deflectable surface; (2) inserting the sensor to a location within the body of a patient at which the sensor can detect pressure within the heart; (3) affixing the sensor relative to the heart; (4) interrogating the sensor with an electromagnetic field; (5) receiving a signal from the sensor corresponding to a sensed pressure; and (6) leaving the sensor in situ so that future pressure measurements can be made.

5 Claims, 2 Drawing Sheets

METHOD FOR USING A WIRELESS PRESSURE SENSOR TO MONITOR PRESSURE INSIDE THE HUMAN HEART

PRIOR RELATED APPLICATIONS

This application claims the priority benefit of U.S. Provisional Patent Application No. 60/818,707 filed Jul. 5, 2006.

TECHNICAL FIELD

The present invention relates generally to methods for sensing pressure within the heart. More specifically, the invention relates to the use of a passive, wireless pressure sensor for sensing pressure within the heart which can remain in situ for taking future pressure measurements without the need for additional invasive procedures.

BACKGROUND OF THE INVENTION

The pressure of blood within the heart is fundamental to the diagnosis, treatment and management of cardiac disease. The standard method of measuring heart pressure is by means of a catheter, a long, thin flexible plastic tube that is directed into the chambers of the heart either through the skin directly or maneuvered through the arteries or veins and positioned within the heart or pulmonary vessels. Because these devices require penetration of the skin and direct physical connection to the measurement instrumentation, they can be left in place only for short periods of time. The need for additional measurements then requires reinsertion of the catheter into the patient.

Thus there is a need for an improved method for measuring pressure within the heart.

There is a further need for a method for measuring pressure within the heart that does not require reinsertion and removal of the measuring device for future measurements of pressure within the heart.

SUMMARY OF THE INVENTION

Stated generally, the present invention comprises a method for measuring pressure within a heart, comprising the steps of: (1) providing a passive wireless pressure sensor having a characteristic impedance and a deflectable surface, the characteristic impedance changing in response to deflection of the deflectable surface; (2) inserting the sensor to a location within the body of a patient at which the sensor can detect pressure within the heart; (3) affixing the sensor relative to the heart; (4) interrogating the sensor with an electromagnetic field; (5) receiving a signal from the sensor corresponding to a sensed pressure; and (6) leaving the sensor in situ so that future pressure measurements can be made.

In various embodiments, the location at which the sensor can detect pressure within the heart includes the left atrium, the right atrium, the left ventricle, the right ventricle, or an exterior wall of the heart. In the latter instance one suitable location on the exterior wall of the heart is the interatrial groove.

In various other embodiments, the sensor can be affixed relative to the heart by suturing the sensor to an internal wall of a heart, suturing the sensor to an external wall of the heart, suturing the sensor within the interatrial groove, or affixing the sensor to another device that has been or will be implanted within the heart.

Thus it is an object of the present invention to provide an improved method for measuring pressure within the heart.

It is another object of the present invention to provide a method for measuring pressure within the heart that does not require reinsertion and removal of the measuring device for future measurements of pressure within the heart.

Other objects, features, and advantages of the present invention will become apparent upon reading the following specification, when taken in conjunction with the drawings and the appended claims.

DETAILED DESCRIPTION OF THE DISCLOSED EMBODIMENT

Figure 1:
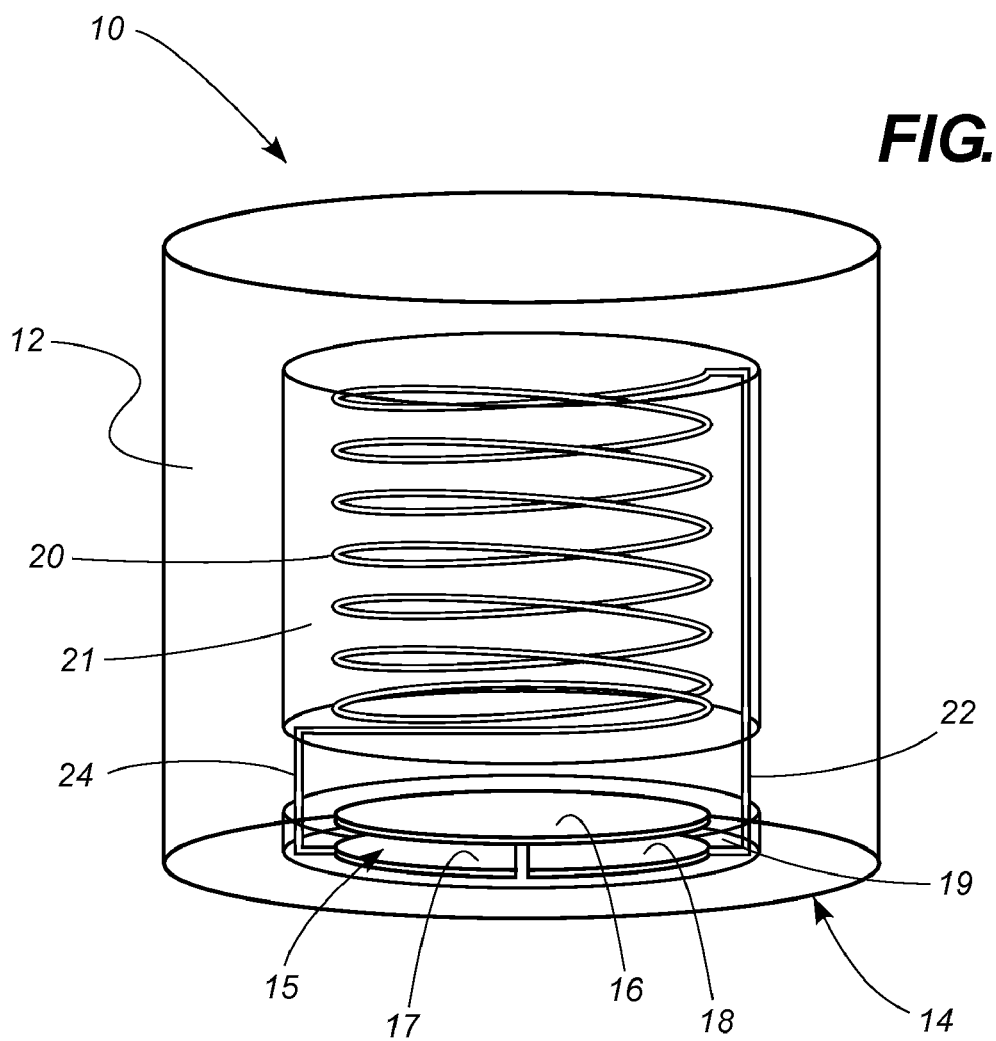
FIG. 1 is a schematic diagram of a human heart in cross-section.

Referring now to the drawings, in which like numerals indicate like elements throughout the several views, FIG. 1 illustrate a wireless, unpowered pressure sensor 10. The sensor 10 includes a body 12. The sensor 10 comprises a deflectable region 14 at the lower end of the body 12. The body 12 further comprises a lower chamber 19 and an upper chamber 21. The body 12 is formed from electrically insulating materials, preferably biocompatible ceramics. In a preferred embodiment, the body is comprised of fused silica.

The sensor 10 can be fabricated using micro-machining techniques and is small, accurate, precise, durable, robust, biocompatible, and insensitive to changes in body chemistry, or biology. Additionally, the sensor 10 can incorporate radiopaque features to enable fluoroscopic visualization during placement within the body. Furthermore, this sensor is encased in a hermetic, unitary package of electrically insulating material where the package is thinned in one region so as to deform under a physiologically relevant range of pressure. The LC circuit contained in the packaging is configured so that one electrode of the capacitor is formed on the thinned region. This sensor does not require the use of external connections to relay pressure information externally and does not need an internal power supply to perform its function. The pressure sensor of the current invention can be attached to the end of a catheter to be introduced into a human body and delivered to an organ or vessel using catheter-based endovascular techniques.

An LC resonator is hermetically housed within the body 12 and comprises a capacitor 15 and an inductor 20. As used herein, the term "hermetic" will be understood to mean "completely sealed, especially against the escape or entry of air and bodily fluids." The capacitor 15 is located within the lower cylindrical chamber 19 and comprises three plates: an upper plate 16, and lower plates 17 and 18. The lower plates 17, 18 are co-planar and are disposed in parallel, spaced apart relation to the upper plate 16. The inductor 20 comprises a coil disposed within the upper chamber 21 and which is in conductive electrical contact with the lower plates 17, 18 of the capacitor 15 via conductors 22, 24.

The lower capacitor plates 17, 18 are positioned on the inner surface of the deflectable region 14 of the sensor body 12. The upper capacitor plate 16 is positioned on a fixed region of the sensor body 12. A change in ambient pressure at the deflectable region 14 of the sensor 10 causes the deflectable region 14 to bend, thereby displacing the lower plates 17, 18 with respect to the upper plate 16 and changing the capacitance of the LC circuit. Because the change in capacitance of the LC circuit changes its resonant frequency, the resonant frequency of the sensor 10 is pressure-dependent.

The disclosed sensor features a completely passive inductive-capacitive (LC) resonant circuit with a pressure varying capacitor. Because the sensor is fabricated using completely passive electrical components and has no active circuitry, it does not require on-board power sources such as batteries, nor does it require leads to connect to external circuitry or power sources. These features create a sensor which is self-contained within the packaging material and lacks physical interconnections traversing the hermetic packaging, such interconnects frequently being cited for failure of hermeticity. Furthermore, other sensing capabilities, such as temperature sensing, can be added using the same manufacturing techniques. For example, temperature sensing capability can be accomplished by the addition of a resistor with known temperature characteristics to the basic LC circuit.

The capacitor in the pressure sensor of the disclosed invention consists of three conductive elements separated by a gap. If a force is exerted on the sensor, the portion 14 of the sensor deflects, changing the relative position between the upper plate 16 and the lower plates 17, 18. This movement will have the effect of reducing the gap between the conductive elements 16-18, which will consequently change the capacitance of the LC circuit. An LC circuit is a closed loop system whose resonance is proportional to the inverse square root of the product of the inductor and capacitor. Thus, changes in pressure alter the capacitance and, ultimately, cause a shift in the resonant frequency of the sensor. The pressure of the environment external to the sensor is then determined by referencing the value obtained for the resonant frequency to a previously generated curve relating resonant frequency to pressure.

Because of the presence of the inductor, it is possible to couple to the sensor electromagnetically and to induce a current in the LC circuit via a magnetic loop. This characteristic allows for wireless exchange of electromagnetic energy with the sensor and the ability to operate it without the need for an on-board energy source such as a battery. Thus it is possible to determine the pressure surrounding the sensor by a simple, non-invasive procedure by remotely interrogating the sensor, recording the resonant frequency, and converting this value to a pressure measurement.

One method of sensor interrogation is explained in U.S. patent application Ser. No. 11/105,294, incorporated herein by reference. According to this invention, the interrogating system energizes the sensor with a low duty cycle, gated burst of RF energy having a predetermined frequency or set of frequencies and a predetermined amplitude. The energizing signal is coupled to the sensor via a magnetic loop. The energizing signal induces a current in the sensor that is maximized when the frequency of the energizing signal is substantially the same as the resonant frequency of the sensor. The system receives the ring down response of the sensor via magnetic coupling and determines the resonant frequency of the sensor, which is then used to determine the measured physical parameter. The resonant frequency of the sensor is determined by adjusting the frequency of the energizing signal until the phase of the ring down signal and the phase of a reference signal are equal or at a constant offset. In this manner, the energizing signal frequency is locked to the sensor's resonant frequency and the resonant frequency of the sensor is known. The pressure of the localized environment can then be ascertained.

Figure 2:
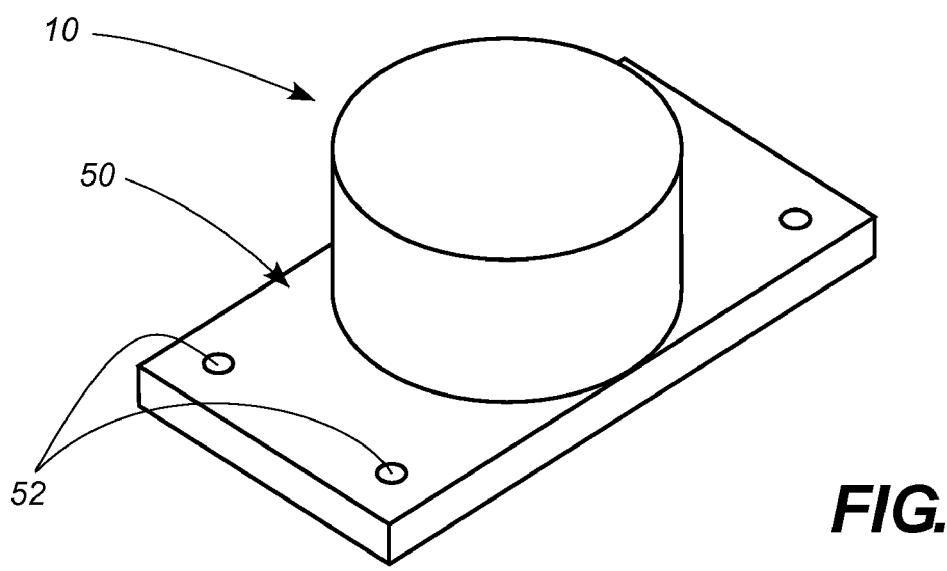
FIG. 2 is an isometric view of an implantable, wireless sensor for measuring heart pressure according to the disclosed embodiments.

FIG. 2 shows the sensor 10 mounted to a planar portion 50. The planar portion 50 includes holes 52 mounted in its outer portions for suturing the sensor 10 to a support structure.

Figure 3:
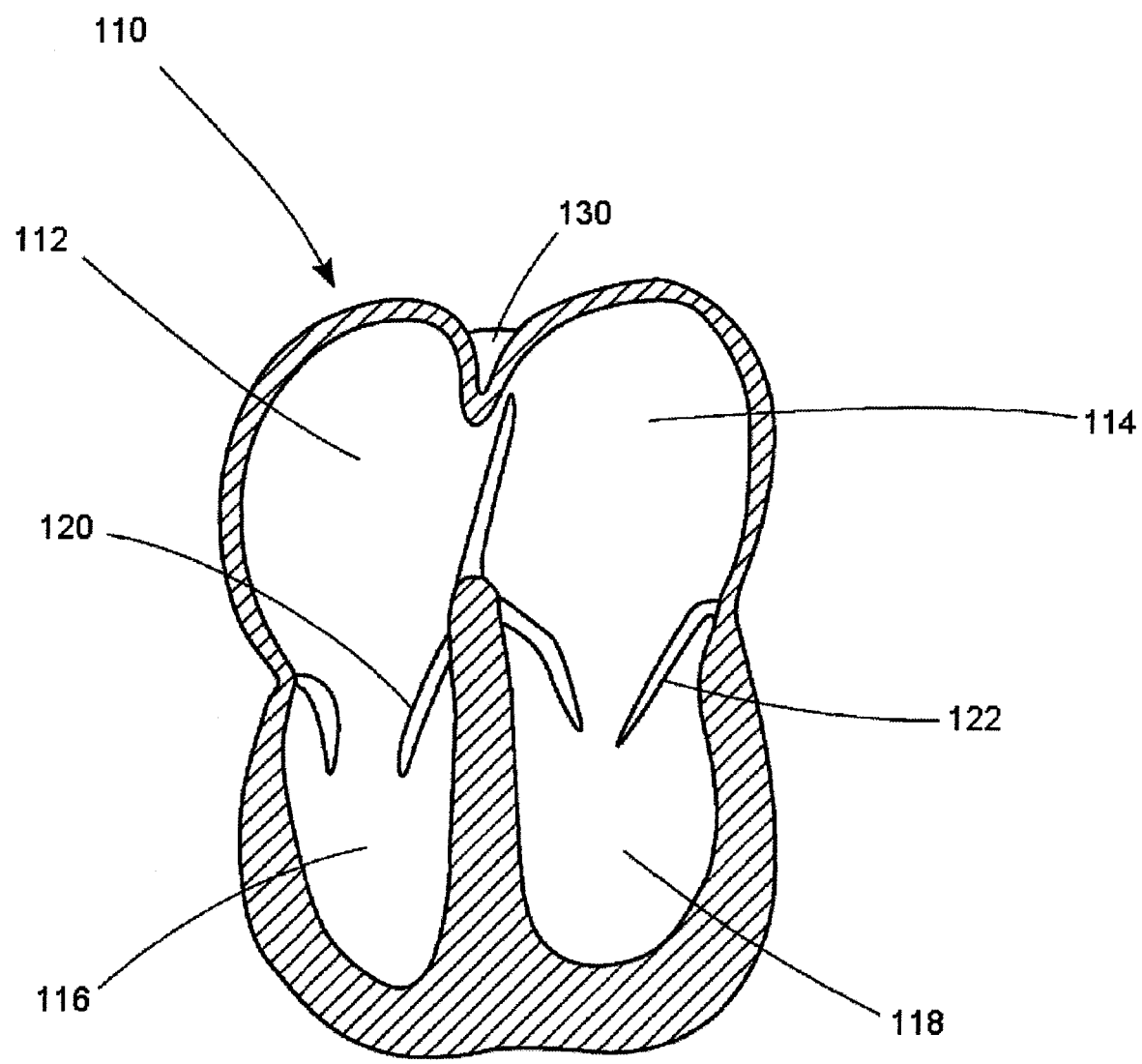
FIG. 3 is a schematic view showing the electronics of the sensor of FIG. 2.

FIG. 3 depicts a human heart 110. The heart has a right atrium 112, a left atrium 114, a right ventricle 116, and a left ventricle 118. The tricuspid valve 120 is a dual-flap valve separating the right atrium 112 from the right ventricle 116, and the mitral valve 122 is a dual-flap valve separating the left atrium 114 from the left ventricle 118. At the upper end of the heart is the interatrial groove 130, an infolding filled with extracardiac fibro-fatty tissue.

The shape and size of the sensor 10 allows it to be placed directly into the heart 110 during cardiac surgery so that pressure measurements can be made at any time following the procedure. Methods for securing the sensor into the heart include suturing into the right or left atrium 112, 114 or the right or left ventricle 116, 118 during open-heart surgery, or introducing the sensor by securing it first to another device being implanted into the heart.

It has also been found that the sensor 10 can be attached to an exterior surface of the heart 110 to measure pressure, rather than being implanted within the heart. The deflective region 14 of the sensor 10 responds predictably to the application of force. Because of the stiffness or lack of compliance of this deflective surface 14, any biological material having a higher compliance that is in contact with the deflective region will allow fluid pressure to transmit through the biological material without any dampening of the pressure waveform. Alternatively, the phenomenon can be explained in terms of Young's Modulus or spring constant. For instance, cardiac tissues have a Young's Modulus of about, e.g., 6-50 kPa, and a fused silica deflective region has a Young's Modulus of about, e.g., 100 GPa. These figures result in a ratio of Young's Modulus between the silica sensor and the biological material of about, e.g., 1-10 MPa. The disclosed invention will be enabled by having a ratio of at least 100, preferably at least 1000, most preferably at least 10,000 and, even more preferably at least 100,000 between the ratios of values of Young's Modulus of the deflective region of the sensor and that of the biological material. Alternatively, well-known models for plates of any geometry clamped around their periphery can be utilized to calculate the maximum deflection for a given geometry and load, from which a spring constant can be calculated. For instance, a deflective region having a 2 mm length, a 2 mm width, a 0.1 mm thickness, a 1 mm Hg load and a 100 GPA Young's Modulus can be used to calculate a maximum deflection of almost $3 \times 10^{-9}$ m. Given the maximum deflection of the plate and the load applied to the plate, the spring constant can be determined via well known mathematical relationships.

The sensor 10 that enables practice of the disclosed methods is preferably passive, i.e., not self-powered. Rather, the sensor is powered by an electromagnetic field created from a location exterior of the patient's body that interrogates the sensor and causes the sensor to send back a signal corresponding to a sensed pressure. Thus there are no power or communications leads running from the sensor to a location outside the patient, and no batteries that need to be replaced periodically.

The sensor 10 can have a width of about 0.5 to about 4 mm, a height of about 0.2 to about 4 mm, and a length of about 0.5 to about 30 mm. In one embodiment, the intracorporeal device has a width of 2 mm, a height of 0.4 mm, and a length of 10 mm. Examples of such devices are disclosed in commonly owned U.S. Pat. No. 6,855,115; and in co-pending, commonly owned U.S. patent application Ser. Nos. 10/054, 671; 10/886,829; 10/215,377; 10/215,379; 10/943,772; and 11/157,375, all of which are incorporated herein by reference.

The consequence of this design is that if the deflective region 14 of the sensor 10 is placed in direct contact with an external surface of the heart 110, pressure changes within the chambers of the heart will be transmitted though the heart wall undampened to a sufficient degree that they provide an accurate measurement of the pressure within the heart. Such an accuracy is, e.g., within a 1 mm Hg tolerance, or as accurate as any catheter or guidewire-based acute pressure sensing system. Thus, highly accurate measurements of heart pressure can be obtained without having to physically open the heart. This feature is highly advantageous in many types of surgery, e.g., coronary bypass procedures.

According to this method, the pressure sensor 10 can be sutured to an exterior wall of the heart 110. One suitable external location for placement of the sensor 10 is in the interatrial groove 130. Also known as Waterson's or Sondergard's groove, this groove 130 separates the right and the left atria 112, 114 as depicted in FIG. 3.

In practice, the interior of the interatrial groove 130 is exposed, and the sensor 10 is located within the open space. Suturing the groove 130 closed both safely secures the sensor 10 and positions the sensor directly on the surface of a part of the heart wall that is in communication with the left atrium 114, thereby allowing for pressure measurement of the internal pressure of the left atrium without having to place the sensor directly in the left atrium.

In situations where the interior of the heart is exposed, such as surgical repair of the mitral or aortic valves, the sensor can be sutured directly to the inner wall of the heart during the procedure. The shape of the sensor 10 combined with its non-thrombogenic surface make it easy and safe to locate the sensor on the inner heart wall. Optionally, laser drilled holes in the sensor 10 at the ends provide a location for standard surgical suture to be introduced in order to secure the sensor to the heart wall.

Furthermore, the small shape of the sensor along with the ability to attach various shaped wire baskets (e.g., nitinol wire baskets) provides a means for attaching it to other implantable devices that can be introduced into the heart. These devices include artificial heart valves, left atrial appendage closure devices, trans-septal occluders, left ventricle assist devices, fully implantable artificial hearts, and annuloplasty rings.

In the case of mitral valve surgery, pressure measurement is useful to assess the function of the new or repaired valve. One of the potential problems with mitral valve repair is that the new or repaired valve may not seal properly, resulting in mitral valve regurgitation as blood flows back into the left atrium when the valve is in its closed state. Normally, this is monitored with the use of trans-esophageal ultrasound. However, this technique requires insertion of an ultrasound transducer mounted on the end of an elongated tube that is inserted into a patient's esophagus. This method is not only unpleasant but can also be an unreliable measurement technique.

The use of the implantable wireless pressure sensor that can detect pressure in the left atrium is highly beneficial, as it allows the physician to obtain important information regarding valve function easily at any time without the need for an additional invasive procedure.

A further application of the technology is surgical attachment into the left atrium during a heart transplant procedure. With a newly transplanted heart there is a primary concern about whether or not the transplanted organ is being rejected. To assess this situation, monthly pressure measurements with a catheter along with trans-catheter biopsy of heart tissue must be performed. By taking regular pressure measurements with an implanted wireless sensor, the physician can assess the function of the new heart without needing to perform a series of invasive procedures.

Once in place within the heart, measurement of pressure can be easily accomplished using wireless communication apparatus and techniques such as those disclosed in U.S. patent application Ser. No. 11/105,294, filed Apr. 13, 2005 and U.S. patent application Ser. No. 11/276,571, filed Mar. 6, 2006, both of which are hereby incorporated by reference.

Finally, it will be understood that the preferred embodiment has been disclosed by way of example, and that other modifications may occur to those skilled in the art without departing from the scope and spirit of the appended claims.

What is claimed is:

1. A method for measuring pressure within a heart, comprising the steps of:
   providing a passive wireless pressure sensor having a characteristic impedance and a deflectable surface, the characteristic impedance changing in response to deflection of the deflectable surface;
   inserting the sensor into the body of a patient to a location proximate to the heart;
   affixing the sensor to the heart at a location on an exterior wall of the heart such that the deflectable surface of the sensor is located outside of the heart and in direct contact with the exterior wall of the heart;
   interrogating the sensor with an electromagnetic field;
   receiving a signal from the sensor corresponding to the characteristic impedance of the sensor, which corresponds to a sensed pressure; and
   leaving the sensor in situ so that future pressure measurements can be made.

2. The method of claim 1, wherein the step of affixing the sensor to the heart at a location on the exterior wall of the heart comprises the step of affixing the sensor to the heart at a location in the interatrial groove of the heart.

3. The method of claim 2, wherein the step of affixing the sensor to the heart at a location in the interatrial groove of the heart comprises the step of suturing the interatrial groove closed.

4. The method of claim 1, wherein the sensed pressure is within about a 1 mm Hg tolerance of the actual pressure within the heart.

5. The method of claim 1, wherein the ratio of values of Young's Modulus of the deflectable surface of the sensor and that of the biological material forming the exterior wall of the heart is at least about 100.

* * * * *